US008049516B2

(12) United States Patent
Hancock et al.

(10) Patent No.: US 8,049,516 B2
(45) Date of Patent: Nov. 1, 2011

(54) APPARATUS AND METHOD FOR DETECTING A DISCONTINUITY WITHIN A NON-BIOLOGICAL ELEMENT LOCATED WITHIN A BIOLOGICAL STRUCTURE

(75) Inventors: Christopher Paul Hancock, Somerset (GB); John Bishop, Swindon (GB); Martin Wynford Booton, Somerset (GB)

(73) Assignees: Creo Medical Llimited, Somerset (GB); Microoncology Limited, Somerset (GB)

( * ) Notice: Subject to any disclaimer, the term of this patent is extended or adjusted under 35 U.S.C. 154(b) by 435 days.

(21) Appl. No.: 12/278,112

(22) PCT Filed: Feb. 5, 2007

(86) PCT No.: PCT/GB2007/000375
§ 371 (c)(1),
(2), (4) Date: Feb. 3, 2009

(87) PCT Pub. No.: WO2007/088386
PCT Pub. Date: Aug. 9, 2007

(65) Prior Publication Data
US 2009/0322349 A1    Dec. 31, 2009

(30) Foreign Application Priority Data
Feb. 3, 2006    (GB) .................................. 0602167.9

(51) Int. Cl.
*G01R 27/04* (2006.01)
(52) U.S. Cl. ...................................................... 324/639
(58) Field of Classification Search .................... None
See application file for complete search history.

(56) References Cited

U.S. PATENT DOCUMENTS

| 2003/0036713 | A1* | 2/2003 | Bouton et al. ................. 600/587 |
| 2004/0065158 | A1* | 4/2004 | Schrepfer et al. .......... 73/864.81 |
| 2004/0077943 | A1  | 4/2004 | Meaney |
| 2004/0254457 | A1  | 12/2004 | Van Der Weide |
| 2008/0319285 | A1* | 12/2008 | Hancock ........................ 600/309 |

FOREIGN PATENT DOCUMENTS

| EP | 0 804 900     | 11/1997 |
| WO | WO 2005/115235 | 12/2005 |
| WO | WO 2006/115485 | 11/2006 |
| WO | WO 2007/003955 | 11/2007 |

OTHER PUBLICATIONS

International Search Report for International Application No. PCT/GB2007/000375 dated Apr. 13, 2007.

* cited by examiner

*Primary Examiner* — Jermele M Hollington
(74) *Attorney, Agent, or Firm* — Marshall, Gerstein & Borun LLP

(57) ABSTRACT

Apparatus for detecting a discontinuity within a non-biological element located within a biological structure, the apparatus comprising: a microwave energy source; a first antenna coupled to the microwave energy source and arranged to transmit the microwave energy into the biological structure; a second antenna arranged to receive at least a portion of the transmitted microwave energy; an antenna carrier arranged to have the first and second antenna affixed thereon and including means for moving the first and second antenna with respect to the biological structure; and a signal processing unit coupled to the second antenna arranged to determine the phase and/or magnitude response of the received microwave energy as a function of the position of the antennas with respect to the biological structure and provide an indication of the location of the discontinuity within the non-biological element according to the phase and/or magnitude response.

35 Claims, 9 Drawing Sheets

HELIX LENGTH = 6 λ

'X' SECTION ALONG SHAFT

SIDE VIEW

APPARATUS AND METHOD FOR DETECTING A DISCONTINUITY WITHIN A NON-BIOLOGICAL ELEMENT LOCATED WITHIN A BIOLOGICAL STRUCTURE

BACKGROUND

In some surgical procedures metallic inserts are inserted into a patients body for the purpose of repairing severe bone fractures and breakages caused, for example, in vehicle accidents. One group of such inserts include metal pins, or cylindrical bars. After implantation one or more locking holes are drilled through the biological tissue structure (skin, fat, bone, etc.) at the distal and proximal ends for the purpose of securing the inserts. Normally, the location, drilling, and locking of proximal holes in the insert is not a major technical challenge, but distal hole interlocking of the inserts is a highly specialised and technically demanding procedure, particularly when it comes to the placement of distal locking screws through a locking hole in the metal inserts.

Traditional techniques for distal locking of inserts include the use of mechanical jigs and the free hand technique, and X-ray machines. The mechanical method is prone to providing inaccurate information and a common problem experienced by surgeons is that once a hole has been inaccurately drilled it is virtually impossible to drill a second hole since the correct position of the hole is normally very close to the existing hole, thus causing the drill to slip and follow the path of the first hole. The use of X-ray machines is time consuming, requires specialised personnel to operate, and presents a risk of staff/patient exposure to potentially harmful doses of ionised radiation.

Distal interlocking is acknowledged as being the most difficult part of the insert insertion procedure. When difficulties are encountered in such a procedure X-ray screening times (exposure to the patient and the surgical team) can be greater than ten minutes, and the operating time can be greater than one hour. Difficulties often arise due to the fact that the radiographer is unable to provide the surgeon with the required image. This is often due to the fact that the surgeon is unable to manipulate the X-ray machine to produce the required image because the machine is not sterile and is cumbersome to use, thus it is physically impossible to place the X-ray head close to the fracture site.

SUMMARY OF THE PRESENT INVENTION

According to a first aspect of the present invention there is provided apparatus for detecting a discontinuity within a non-biological element located within a biological structure, the apparatus comprising:
  a microwave energy source;
  a first antenna coupled to the microwave energy source and arranged to transmit the microwave energy into the biological structure;
  a second antenna arranged to receive at least a portion of the transmitted microwave energy;
  an antenna carrier arranged to have the first and second antenna affixed thereon and including means for moving the first and second antenna with respect to the biological structure; and
  a signal processing unit coupled to the second antenna and arranged to determine the phase and/or magnitude response of the received microwave energy as a function of the position of the antennas with respect to the biological structure and provide an indication of the location of the discontinuity within the non-biological element according to the phase and/or magnitude response.

Further variations to this apparatus may be made within the scope of the appended dependent claims 2 to 16.

According to a second aspect of the present invention there is provided a method of detecting a discontinuity within a non-biological element located within a biological structure, the method comprising:
  transmitting microwave energy into the biological structure from a first antenna;
  receiving at least a portion of the transmitted microwave energy at a second antenna;
  moving the first and second antenna with respect to the biological structure; and
  measuring the received microwave energy and determining the phase and/or magnitude response of the received microwave energy as a function of the position of the antennas with respect to the biological structure and providing an indication of the location of the discontinuity within the non-biological element according to the phase and/or magnitude response.

Further variations to this method may be made within the scope of the appended dependent claims 18 to 31.

DETAILED DESCRIPTION OF EMBODIMENTS OF THE INVENTION

Figure 1:
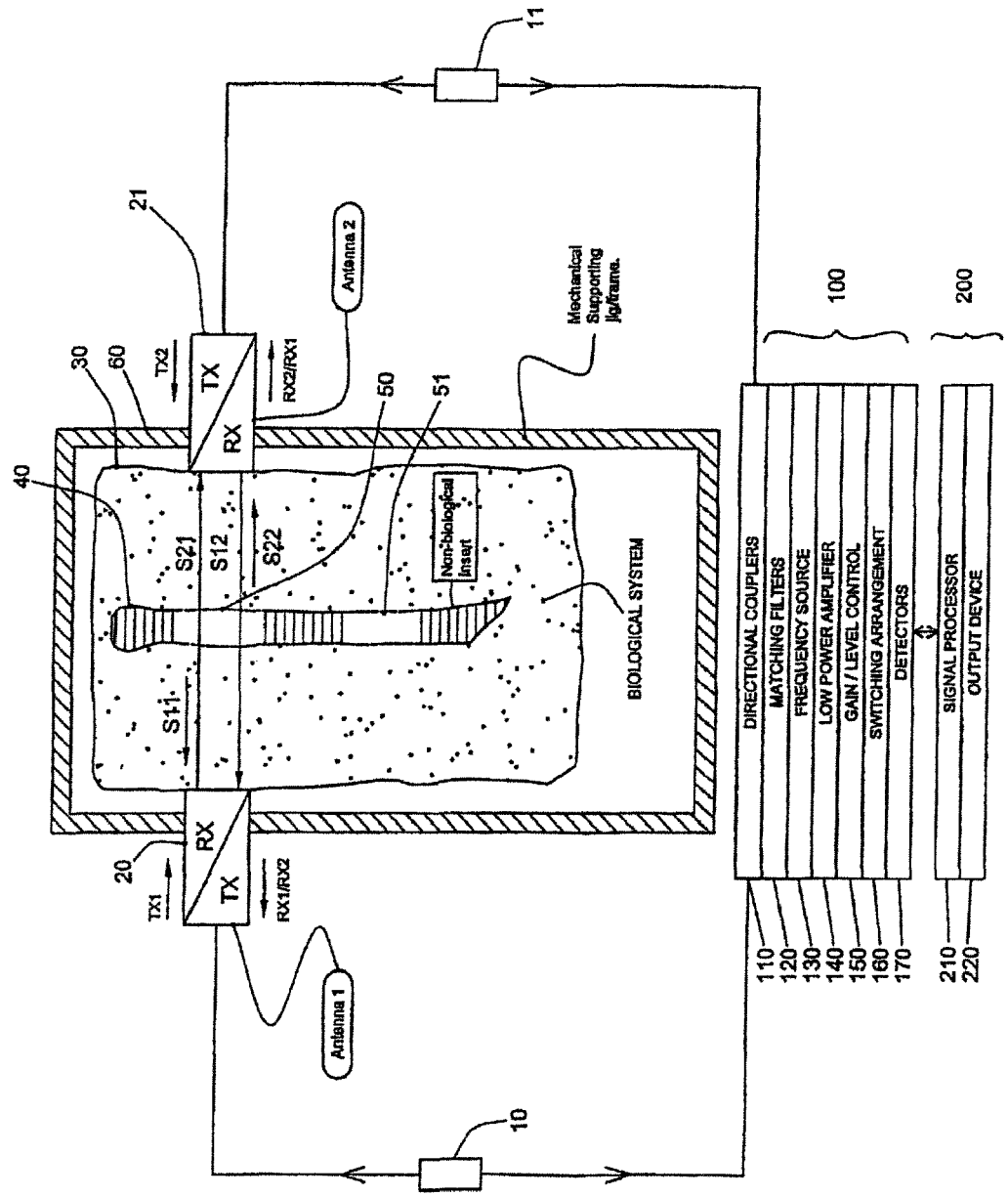
FIG. 1 schematically illustrates apparatus according to an embodiment of the present invention.

Turning now to the drawings, a diagram schematically illustrating an embodiment of the invention is shown in FIG. 1. Two transmit/receive antennas 20 and 21 are provided in contact with the biological structure 30 of interest that contains a surgical insert 40 (shown in FIG. 1 as an intramedullary nail) with two discontinuities 50, 51 (shown in FIG. 1 as locking holes) that are depicted as holes or channels in the insert 40. A frame, or jig, 60 is also shown that is provided to keep the two antennas aligned. The frame/jig could be a similar arrangement to that used in conventional alignment procedures, such as those performed by orthopaedic surgeons where fractured or broken bones require precision alignment.

A system of microwave elements are provided, illustrated in FIG. 1 as a single block 100. The microwave elements preferably include frequency source(s) 130, a low-power amplifier arrangement 140, adjustable gain/level control 150, antenna matching filters 120, electronic switching arrangements 160, directional couplers 110 and a detection scheme 170. Each element is discussed in detail below and specific embodiments are given. A signal processing unit 210 and display (or other suitable output device) 220 are also provided and are illustrated in FIG. 1 as a single block 200. These elements are also discussed in more detail later in the description.

It may be preferable for the two antennas 20,21 to have a narrow beam-width, for example, less than 20°, to enable the transmitted signal to be focussed towards the receiving antenna. In this instance it may also be preferable that antennas 20,21 are helical or inverted horn constructions. Transmission cables 10, 11 are used as the preferred means of transferring energy between the two antennas 20,21 and the directional couplers 110. Preferably the cables take the form of co-axial, or flexible waveguide assemblies, but other transmission means may be apparent to the person skilled in the art. In this invention it is preferred to keep antennas 20,21 separate from the microwave elements 100 and the signal processor 210 and output device 220 (200). It is also preferable that elements 100 and 200 are contained together in a single enclosure, and the enclosure is positioned in a location that is in isolation from the biological system 30. In this way the electronic instrumentation, which may not be sterile, is kept away from a potentially sterile environment where there is a possibility of the unit being sprayed with fluid, such as blood or saline.

The arrangement illustrated in FIG. 1 allows for a full 2-port scattering matrix to be constructed from the transmitted and reflected signals, measured using directional couplers 150, to provide the information necessary to locate the object or discontinuity in the object. The standard two port scattering parameter measurement notation is shown in FIG. 1, where $S_{21}$ represents the transmission through the biological and non-biological systems 30,40 from antenna 1 (20) to antenna 2 (21), $S_{12}$ represents the transmission through the biological and non-biological systems 30,40 from antenna 2 (21) to antenna 1 (20), $S_{11}$ represents the reflection measurement from energy being reflected at the interface between the biological and non-biological 30,40 system back along the path towards antenna 1 (20), and $S_{22}$ represents the reflection measurement from energy being reflected at the interface between the biological and non-biological system 30,40 back along the path towards antenna 2 (21).

Table 1 (below) lists the defining properties for a biological structure to which embodiments of the present invention may be applied, namely: conductivity ($\sigma$), relative permittivity ($\epsilon_r$), loss factor (tan $\delta$), wavelength in tissue material ($\lambda$), and penetration depth (D), and how these properties change as a function of frequency. The tissue types listed here are: dry skin, wet skin, fat, blood, cartilage, muscle, cancellous bone, cortical bone and marrow bone and the properties are given for seven spot frequencies, namely: 2 GHz, 5 GHz, 5.2 GHz, 7 GHz, 10 GHz, 18 GHz and 70 GHz. The parameters listed in Table 1 can be used to calculate the complex impedance associated with each tissue at a specific frequency, from which relative phase and magnitude information can be calculated. These parameters can also be used to calculate the transmission (insertion) loss through the complete biological structure 30, and the signal reflections caused by the signal meeting the various tissue boundaries and being partly reflected at the boundary and partly transmitted through the tissue. These calculations are used to establish the signal levels required to ensure that the signal passes through the biological structure and is of high enough strength when it impinges on receive antennas 20, 21 to allow the microwave detection system 100 to differentiate the signal level 1 from the noise level, i.e. it has a high enough signal-to-noise ratio (SNR) to allow the signal level to be discerned from the noise floor.

| Tissue | Conductivity (S/m) | Permittivity ($\epsilon_r$) | Tan $\delta$ | Wavelength (mm) | Penetration Depth (mm) |
|---|---|---|---|---|---|
| 2 GHz | | | | | |
| Dry skin | 1.2654 | 38.568 | 0.29489 | 23.884 | 26.33 |
| Wet skin | 1.3356 | 43.52 | 0.27582 | 22.513 | 26.466 |
| Fat | 0.085918 | 5.3276 | 0.14494 | 64.773 | 142.99 |
| Blood | 2.1861 | 59.022 | 0.3329 | 19.253 | 18.906 |
| Cartilage | 1.423 | 39.759 | 0.32169 | 23.478 | 23.818 |
| Muscle | 1.4538 | 53.29 | 0.2452 | 20.383 | 26.853 |
| Bone Cancellous | 0.6522 | 19.086 | 0.30712 | 33.922 | 35.968 |
| Bone Cortical | 0.31007 | 11.654 | 0.23914 | 43.604 | 58.856 |
| Bone Marrow | 0.07615 | 5.3478 | 0.12798 | 64.687 | 161.54 |
| 5 GHz | | | | | |
| Dry skin | 3.0608 | 35.774 | 0.3076 | 9.9107 | 10.493 |
| Wet skin | 3.5744 | 39.611 | 0.3244 | 9.4068 | 9.4666 |
| Fat | 0.2422 | 5.0291 | 0.17315 | 26.638 | 49.333 |
| Blood | 5.3951 | 53.95 | 0.35952 | 8.0381 | 7.3398 |
| Cartilage | 4.0855 | 33.625 | 0.4368 | 10.112 | 7.7049 |
| Muscle | 4.0448 | 49.54 | 0.29353 | 8.4302 | 9.3347 |
| Bone Cancellous | 1.8116 | 16.05 | 0.40579 | 14.679 | 11.97 |
| Bone Cortical | 0.96228 | 10.04 | 0.34459 | 18.656 | 17.731 |
| Bone Marrow | 0.23379 | 5.0379 | 0.16683 | 26.621 | 51.143 |
| 5.2 GHz | | | | | |
| Dry skin | 3.2185 | 35.61 | 0.31224 | 9.5481 | 9.9594 |
| Wet skin | 3.7611 | 39.364 | 0.33028 | 9.0693 | 8.9727 |
| Fat | 0.2547 | 5.0104 | 0.17572 | 25.658 | 46.837 |
| Blood | 5.6652 | 53.6 | 0.36537 | 7.7505 | 6.9705 |
| Cartilage | 4.2856 | 33.25 | 0.44556 | 9.7695 | 7.3101 |
| Muscle | 4.2669 | 49.278 | 0.29932 | 8.1242 | 8.8291 |
| Bone Cancellous | 1.8954 | 15.881 | 0.41256 | 14.18 | 11.388 |
| Bone Cortical | 1.0101 | 9.946 | 0.35107 | 18.013 | 16.821 |
| Bone Marrow | 0.24633 | 5.0189 | 0.16966 | 25.643 | 48.454 |
| 7 GHz | | | | | |
| Dry skin | 4.8175 | 34.084 | 0.36296 | 7.2215 | 5.2133 |
| Wet skin | 5.5823 | 37.146 | 0.38591 | 6.904 | 6.5352 |
| Fat | 0.37353 | 4.8476 | 0.19789 | 19.358 | 31.443 |
| Blood | 8.2972 | 50.397 | 0.42278 | 5.9076 | 4.6384 |
| Cartilage | 6.1078 | 30.072 | 0.52156 | 7.5716 | 4.9163 |
| Muscle | 6.4607 | 46.865 | 0.35401 | 6.163 | 5.7101 |
| Bone Cancellous | 2.6512 | 14.502 | 0.46948 | 10.963 | 7.8223 |
| Bone Cortical | 1.4431 | 9.171 | 0.40406 | 13.872 | 11.357 |
| Bone Marrow | 0.36563 | 4.8541 | 0.19342 | 19.349 | 32.138 |
| 10 GHz | | | | | |
| Dry skin | 8.0138 | 31.29 | 0.46038 | 5.2291 | 3.7979 |
| Wet skin | 8.951 | 33.528 | 0.47989 | 5.0416 | 3.5267 |
| Fat | 0.58521 | 4.6023 | 0.22857 | 13.885 | 19.586 |
| Blood | 13.131 | 45.109 | 0.52326 | 4.3267 | 2.8013 |
| Cartilage | 9.0229 | 25.63 | 0.63281 | 5.6675 | 3.1122 |
| Muscle | 10.626 | 42.764 | 0.44666 | 4.479 | 3.344 |
| Bone Cancellous | 3.8591 | 12.661 | 0.54789 | 8.1445 | 5.0636 |
| Bone Cortical | 2.1359 | 8.1197 | 0.47284 | 10.252 | 7.2681 |
| Bone Marrow | 0.57788 | 4.607 | 0.22548 | 13.88 | 19.841 |
| 18 GHz | | | | | |
| Dry skin | 17.176 | 23.649 | 0.72531 | 3.2396 | 1.589 |
| Wet skin | 17.772 | 25.384 | 0.69915 | 3.1375 | 1.5857 |

-continued

| Tissue | Conductivity (S/m) | Permittivity (εr) | Tan δ | Wavelength (mm) | Penetration Depth (mm) |
|---|---|---|---|---|---|
| Fat | 1.1337 | 4.0997 | 0.27615 | 8.1497 | 9.5699 |
| Blood | 25.519 | 33.318 | 0.76488 | 2.715 | 1.2762 |
| Cartilage | 15.129 | 17.992 | 0.83972 | 3.6569 | 1.5982 |
| Muscle | 22.067 | 32.98 | 0.6682 | 2.7635 | 1.4499 |
| Bone Cancellous | 6.5151 | 9.5509 | 0.68122 | 5.1268 | 2.6471 |
| Bone Cortical | 36411 | 6.329 | 0.57452 | 6.3804 | 3.8059 |
| Bone Marrow | 1.1273 | 4.1025 | 0.27442 | 8.1479 | 9.6258 |
| 70 GHz | | | | | |
| Dry skin | 37.577 | 7.0383 | 1.371 | 1.3902 | 0.43524 |
| Wet skin | 41.706 | 9.1213 | 1.1741 | 1.2578 | 0.43343 |
| Fat | 3.0436 | 3.0477 | 0.25645 | 2.4336 | 3.0696 |
| Blood | 57.585 | 10.804 | 1.3687 | 1.1224 | 0.35176 |
| Cartilage | 28.816 | 7.4079 | 0.99891 | 1.4324 | 0.55081 |
| Muscle | 56.036 | 11.308 | 1.2725 | 1.1131 | 0.36452 |
| Bone Cancellous | 14.036 | 4.7263 | 0.7626 | 1.8542 | 0.87363 |
| Bone Cortical | 7.6489 | 3.6282 | 0.54137 | 2.1751 | 1.3666 |
| Bone Marrow | 3.0399 | 3.0486 | 0.25606 | 2.4333 | 3.0737 |

Figure 2:
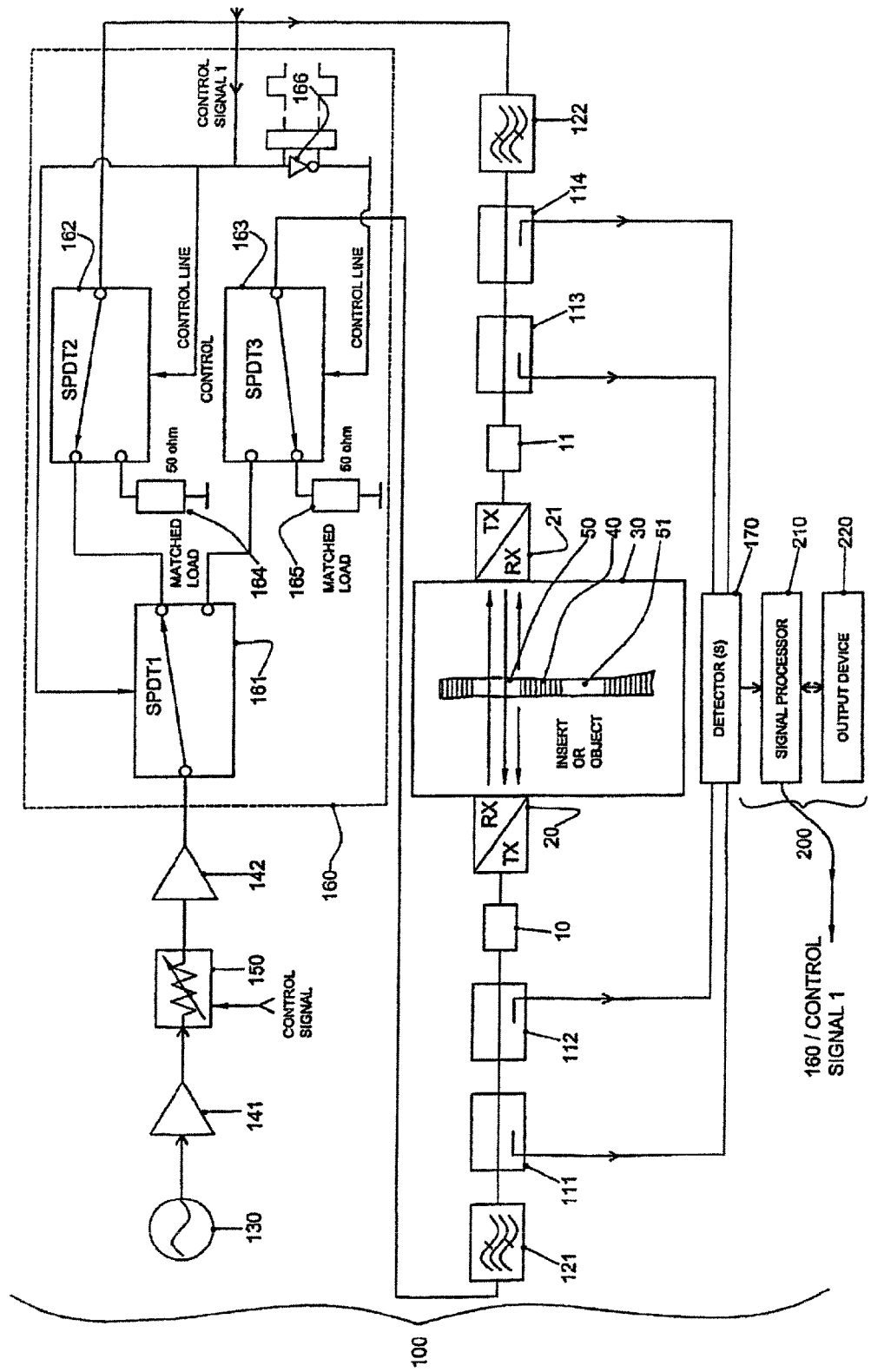
FIG. 2 shows an arrangement for a single frequency measurement system according to an embodiment of the present invention.

The electrical and microwave design elements of an embodiment of the invention are shown in FIG. 2. FIG. 2 shows the arrangement for a single frequency measurement system. A single frequency source 130 is provided, which is preferably a very low power device, for example 0 dBm (1 mW), device and is preferably a stable source derived from a voltage controlled oscillator (VCO), but is not limited to such. A first preamplifier, or buffer, 141 is connected between the frequency source 130 and a gain/level control device 150. The first preamplifier provides some gain and acts as a buffer for the frequency source. The power level produced by the first preamplifier may be in the region of 10 dBm (10 mW) and the device used may be a GaAs fet device, but is not limited to such. The gain/level control device 150 is used to control the power level launched into the transmit antenna 20, 21 and may be a PIN diode attenuator, but is not limited to such. More specifically, an absorptive or reflective device may be used and the control may either be in the form of a digital or an analogue input signal. A second amplifier 142 is connected between the gain/level control device 150 and the input to an electronic switching arrangement 160. Again, a GaAs fet device may be used, but this invention is not limited to using this particular device technology. The power level delivered at the output of 142 may be in the region of 20 dBm (100 mW). This level would be most appropriate when the apparatus is operated at a frequency in the range of between 1 GHz and 10 GHz and the thickness of the biological tissue structure being considered is in the region of between 10 cm and 15 cm. The power budget must be such that there is enough received energy once the signal has passed through the biological tissue structure and the channel in the insert 40 (transmission mode operation) or it has passed through the biological tissue structure and is reflected back at the tissue/insert 30/40 interface (reflection mode operation).

It should be noted that this invention is not limited in terms of the order of the components presented in this description. The order may be changed to provide the most suitable line-up and certain blocks may be omitted where their function becomes redundant, i.e. it may be sufficient to use one amplifier rather than two.

The switching arrangement 160 shown in FIG. 2 enables a single source 130, a low power amplifier chain 141, 142 and a gain/level control device 150 to be used to transmit energy in both directions (bi-directional operation) if antennas 20,21 are reciprocal devices. The first element of the bidirectional switching arrangement is a first electrically controlled single-pole-double-throw (SPDT) switch (SPDT1) 161. The single input to this switch 161 is connected to the output of the second amplifier 142. The first output of the switch 161 is connected to the first output of a second electrically controlled SPDT switch (SPDT2) 162 and the second output of the first switch 161 is connected to the first output of a third electrically controlled SPDT switch (SPDT3) 163. The second output of the second electrically controlled SPDT switch (SPDT2) 162 is connected to a matching load (in this embodiment 50 Ohm) 164, whose function is to ensure that any signal travelling towards the input of the second switch 162 to the second output is absorbed and not reflected back towards the input path. The reflection condition may arise if there is a mismatch at the interface between the aperture of antenna 20,21 and the biological tissue structure 30, or there is a physical break along the path between the proximal end of the antenna 20,21 and the input to a third switch 163. The second output of the third electrically controlled SPDT switch (SPDT3) 163 is connected to a further matching load (50Ω) 165, whose function is to ensure that any signal travelling towards the input of the third switch 163 to the second output is absorbed and not reflected back towards the input path. A control signal is used to select which antenna 20, 21 is to be used as a transmitter and which antenna 20,21 is to be used as a receiver. The control signal is derived from a signal processor 210. Control signals to the first and second SPDT switches (SPDT1, SPDT2) 161, 162 are driven directly from the signal processor 210 and the control signal to the third SPDT switch (SPDT3) is inverted, using a logic inverter 166. Assuming a logic high state connects the single input to the first output, and that a logic low state connects the single input to the second output, if the signal processor 210 sets the control line to logic high state then the input of the first SPDT switch (SPDT1) 161 is connected to the first output, and the first output of the second SPDT switch (SPDT2) 162 is connected to the input, whilst the second output of the third SPDT switch (SPDT3) 163 is connected to the matched load 165. In this condition the transmit antenna is 21 and the receiver is 20. If the logic state from signal processor 210 is reversed then the transmit antenna becomes 20 and the receive antenna 21. The inversion may also take place inside the logic core of the signal processor 210, which maybe an field programmable logic array (FPGA) device, although is not limited to such.

The switching arrangement introduced here is not limited to using electronically controlled SPDT switches. Other devices known to those experienced in the art can also be used. This invention focuses on using the electronically controlled SPDT switches due to ease of configuration, fast speed of operation (contact switching) and availability.

The output signals from the switching arrangement 160 are connected to first and second matching filters 122 and 121 respectively. The purpose of the filters is to ensure that the antennas 20,21 are matched to the impedance of the outer/inner tissue contained in the biological structure 30 in accordance with whether or not it is necessary for the antenna 20,21 to be in contact with the outer skin surface of the biological structure 30, or it is necessary for the energy to be launched through a guide tube 70, whereby the distal aperture of the antenna 20,21 will be in contact with an inner tissue layer of the biological structure 30. In this instance, it will be required for the outer diameter of the antenna 20,21, to be similar to that of the inside diameter of the guide tube 70. The two antennas 20,21 are connected to the output ports of two reverse power directional couplers 112, 113 via flexible co-axial or waveguide cable assemblies 10, 11 to enable all other electronic instrumentation 100,200 to be located in isolation from the a biological tissue structure 30. In a portable unit it may be preferable to connect 20,21 directly to 112,113. It should be noted that in this invention the position of the microwave elements is not restricted in any way to the specific arrangement given in FIG. 6.

The outputs of matching filters 121, 122 are connected to the inputs of respective directional couplers 111, 112, 113 and 114. In the arrangement shown in FIG. 6, the output of first filter 121 connects to the input of first coupler 111, which is a forward power directional coupler, and the output of the first coupler 111 connects to the input of a second coupler 112, which is a reverse power directional coupler. The output of the second coupler 112 is connected to the input of first antenna 20. The output of the second filter 122 connects to the input of a fourth coupler 114, which is a forward power directional coupler, the output of which is connected to the input of a third coupler 113, which is a reverse power directional coupler. The output of the third coupler 113 is connected to the input of the second antenna 21. In the arrangement shown in FIG. 6 forward transmission is from the first antenna 20 to the second antenna 21, the first directional coupler 111 measures the forward transmitted power ($P_{ft}$), the third directional coupler 113 measures the forward received power ($P_{rt}$), and the ratio of $P_{rt}/P_{ft}$ gives the transmission measurement in one direction ($S_{21}$), whilst the second directional coupler 112 measures the reflected received forward power ($P_{fr}$), which provides information regarding the reflection at the various boundaries contained inside the biological system 30 and, the insert 40. This measure equates to an $S_{11}$ measurement. If the signal processor 210 were to change the logic level on the control line, then it would be possible to also measure $S_{12}$ and $S_{22}$ for the opposite direction in a similar manner. Thus this invention enables automated full two port S parameter measurements to be performed.

Signals taken from the directional couplers 111, 112, 113 and 114 are fed into a detector 170. The detector 170 enables the signals to be transformed into voltage levels that represent the magnitude and relative phase of the signals. The detector 170 is controlled by the signal processor 210 and the measured signals from the detector 170 are input to the signal processor 210 whereby are mathematically manipulated and output to an output device 220 in a form that is useful to a user or operator.

The signal processor 210 is used to control the power level output from the second amplifier 142. It also controls the selection of the measurement direction and is responsible for providing system shutdown and error reporting. The signal processor 210 may take the form of a microprocessor or, a combination of logic devices, a digital signal processing unit and a microprocessor core, an FPGA, or another suitable arrangement known to a person well versed in the art. The output device 220 contains user functions and may take the form of monitor and keyboard, an audible sound system or a touch screen device.

Figure 3:
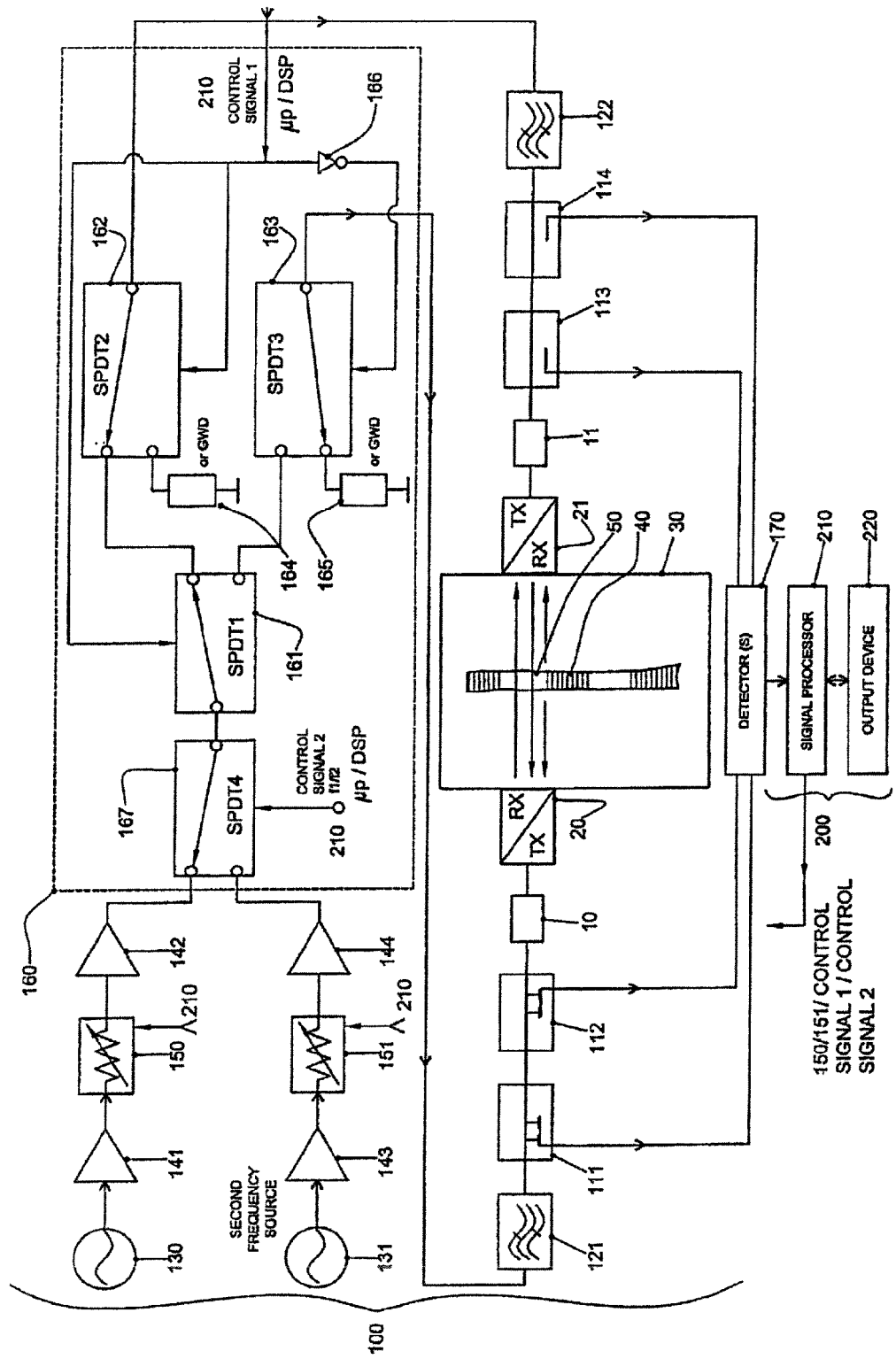
FIG. 3 shows an embodiment of the invention where two frequency sources are used.

FIG. 3 shows an embodiment of the invention whereby two frequency sources 130, 131, and associated signal amplification blocks 141, 142, 143, 144 and gain/level control devices 150,151 are used. One frequency source 130 (131) is used for the purpose of measuring transmission in both directions ($S_{21}$ and $S_{12}$) and the other frequency source 131 (130) is used to measure reflection at the interface between the biological tissue 30 and the non-biological object 40 for each of the two antennas 20,21 ($S_{11}$ and $S_{22}$). The rationale behind using two frequency sources is that in order to transmit the microwave signal through a small discontinuity (hole) 50, a higher frequency may be required than that needed to produce a reflection between the biological system 30 and the discontinuity (hole) 50 that forms a part of the non-biological object (insert) 40. The arrangement of frequency source, amplifier/buffer, gain/level control device and second amplifier for each of the first and second frequency sources is the same as for the arrangement shown in FIG. 2.

The switching arrangement 160 for the dual frequency source arrangement shown in FIG. 3 contains a fourth electronically controlled SPDT switch (SPDT4) 167 that provides the ability to switch between the first and second frequency sources. The remaining components shown in FIG. 3 have already been addressed in the detailed description given for FIG. 2.

Figure 4:
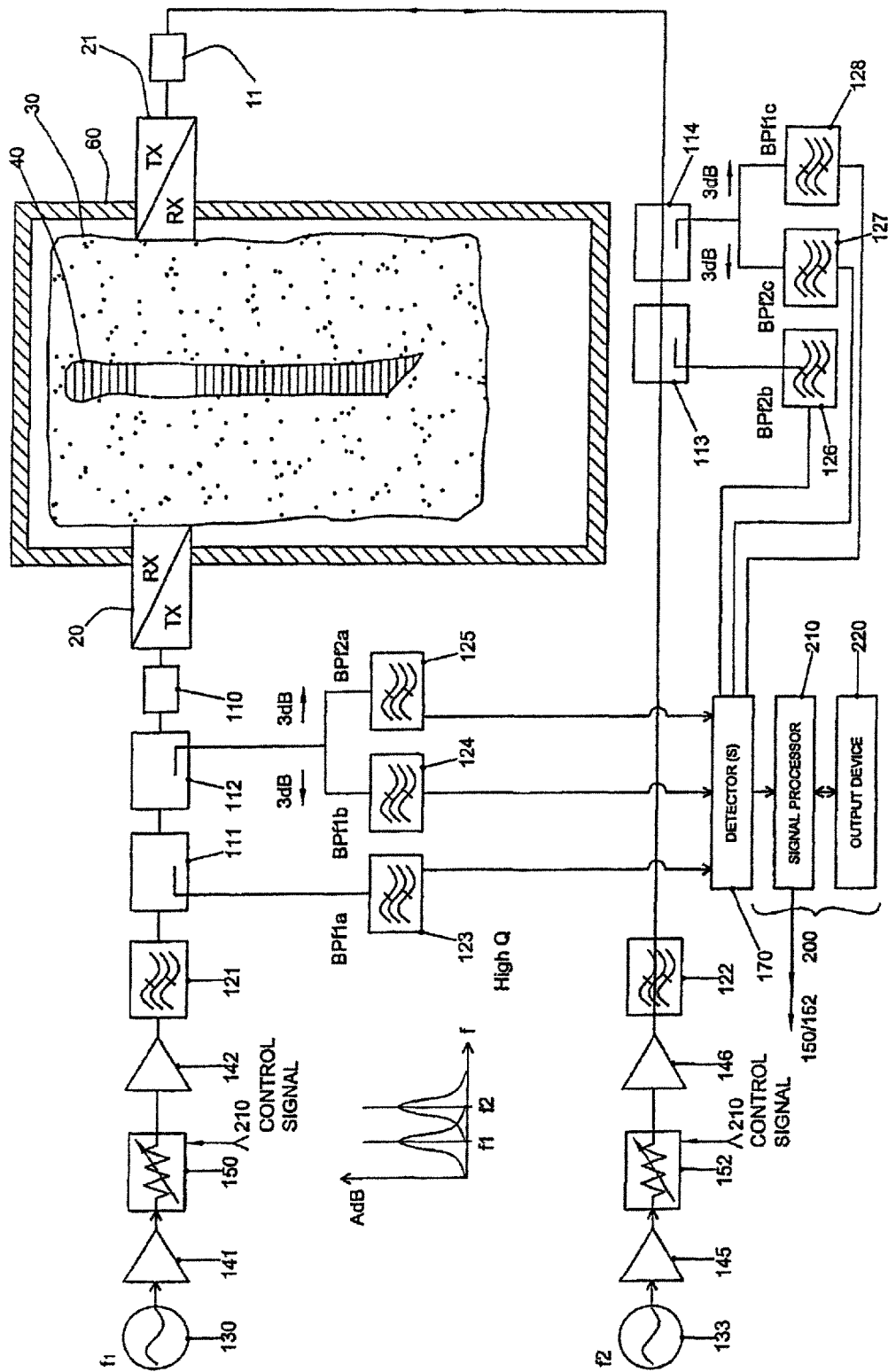
FIG. 4 shows an arrangement in which the switching arrangement shown in FIGS. 2 and 3 is replaced by six high Q, sharp roll-off, band-pass filters.

An alternative microwave configuration is shown in FIG. 4 where the previously illustrated switching arrangement 160 has been replaced by six high Q, sharp roll-off, band-pass filters: $BP_{f1a}$ 123, $BP_{f1b}$ 124, $BP_{f1c}$ 128, $BP_{f2a}$ 125, $BP_{f2b}$ 126, and $BP_{f2c}$ 127. Like components in FIGS. 2 & 3 are numbered alike in FIG. 4. In this context, Q is defined as the frequency being passed through the network divided by the difference between the upper and lower half power frequencies, or −3 dB, frequencies. In this case, it is preferred that the frequency produced by the first frequency source 130 and the frequency produced by the second frequency source 131 are close together in frequency space, but the invention is not limited to this being the case. If this is the case then the band-pass filters preferably exhibit a sharp roll-off, for example 160 dB/decade, to enable the frequency of interest, f1 or f2, to pass through whilst the other frequency, f1 or f2, is rejected to such a level that it does not cause interference to the measured signal, that may otherwise be manifested as distortion of the phase or magnitude of the signal that is required to be passed through the band-pass filter network.

If the two frequencies f1, f2, generated by the first and second frequency source 130, 131 are similar, the operation of the system is similar to that presented for the description of the arrangement shown in FIG. 2. There may be advantages gained from making the first and second frequency source 130, 131 far apart in frequency space. For example, in certain applications it may be required to measure the transmission characteristic for an insert 40 containing a discontinuity 50 which is a hole of small diameter, in which case, one of the frequency sources 130,131 could be of much higher frequency than the other. In this instance, the lower frequency source 130, 131 could be used to make a reflection measurement. Also, in this case, the higher frequency source 130,131 could also be used to make a reflection measurement, but the higher frequency source will be limited by absorption distance inside the biological tissue structure 30 and so if the biological structure 30 is asymmetrical in terms of the location of the non-biological insert 40, then it may be difficult to measure the received signal if the higher frequency source 130,131 and associated antenna 20,21 is located on the far side. This situation may arise when the first antennas 20,21 is located on the surface of the biological structure, and the second antenna 20,21 is positioned inside a guide tube 70, and the guide tube is positioned in close proximity with the non-biological object (insert) 40.

In the arrangement shown in FIG. 4, the coupled port of the first forward power directional coupler 111 feeds into the input of a first band-pass filter $BP_{f1a}$ 123, whose function is to allow the forward signal derived from 130 to pass, but reject any other signals present. If the directivity of the first forward power directional coupler 111 is very high, i.e. is above 20 dB, then first band-pass filter $BP_{f1a}$ 123 would not be required since the directivity of the first coupler 111 will govern the contribution of energy derived from the second frequency source 133 that gets transmitted along this path. The coupled port of the first reverse power directional coupler 112 feeds into the input of second and third band-pass filters $BP_{f1b}$ 124, $BP_{f2b}$ 125 and the outputs from these band-pass filters are fed into the detector 170. In a preferred embodiment, a 3 dB splitter (not shown) may be used between the coupled port of the coupler 112 and the inputs to the second and third filters 124 and 125 to enable the power from the coupler 112 to be split evenly and to prevent signal reflections caused by impedance mismatch that may be caused if such a splitter was not present. The function of second filter $BP_{f1b}$ 124 is to allow for the reflected power from the first energy source derived from first frequency source to pass through and be measured whilst energy from the second energy source, caused by transmission from the second antenna 21 to the first antenna 20, is rejected. The function of the third filter $BP_{f2a}$ 125 is to allow for the transmitted power from the second energy source to pass through and be measured whilst energy from the first energy source, caused by reflection from the biological tissue structure 30 and the non-biological object 40 travelling back along the path of the first antenna 20 and the directional coupler 112, is rejected.

The coupled port of the second forward power directional coupler 113 feeds into the input to the fourth band-pass filter $BP_{f2b}$ 126, whose function is to allow the forward signal derived from the second frequency source 133 to pass through the device, but reject any other out of band signals that may be present. If the directivity of the directional coupler 113 is high enough, i.e. is above 20 dB, then 126 is not be required since the directivity of 113 would govern the contribution of energy, derived from 130, that gets transmitted along this path. The output from fourth filter $BP_{f2b}$ 126 is fed into the detector 170. The coupled port of the second reverse power directional coupler 114 feeds into the input of the fifth and sixth band-pass filters $BP_{f2c}$ 127, $BP_{f1c}$ 128 and the outputs from the band-pass filters are fed into detector 170. In a preferred embodiment a 3 dB splitter may be used between the coupled port of 114 and the inputs to 127 and 128 to enable the power from 114 to be split evenly and to prevent signal reflections caused by impedance mismatch that may be present if such a splitter was not present; the power splitter is not shown in this figure. The function of fifth filter $BP_{f2c}$ 127 is to allow for the reflected power from the second energy source derived from f2 133 to pass through and be measured whilst energy from the first energy source, caused by transmission from the first antenna 20 to second antenna 21, is rejected. The function of sixth filter $BP_{f1c}$ 128 is to allow the transmitted power from the first energy source derived from f1 130 to pass through and be measured whilst energy from the second energy source, caused by reflection from the biological tissue structure 30 and the non-biological object 40 travelling back along the path of the first antenna 20 and directional coupler 114, is rejected.

Figure 5:
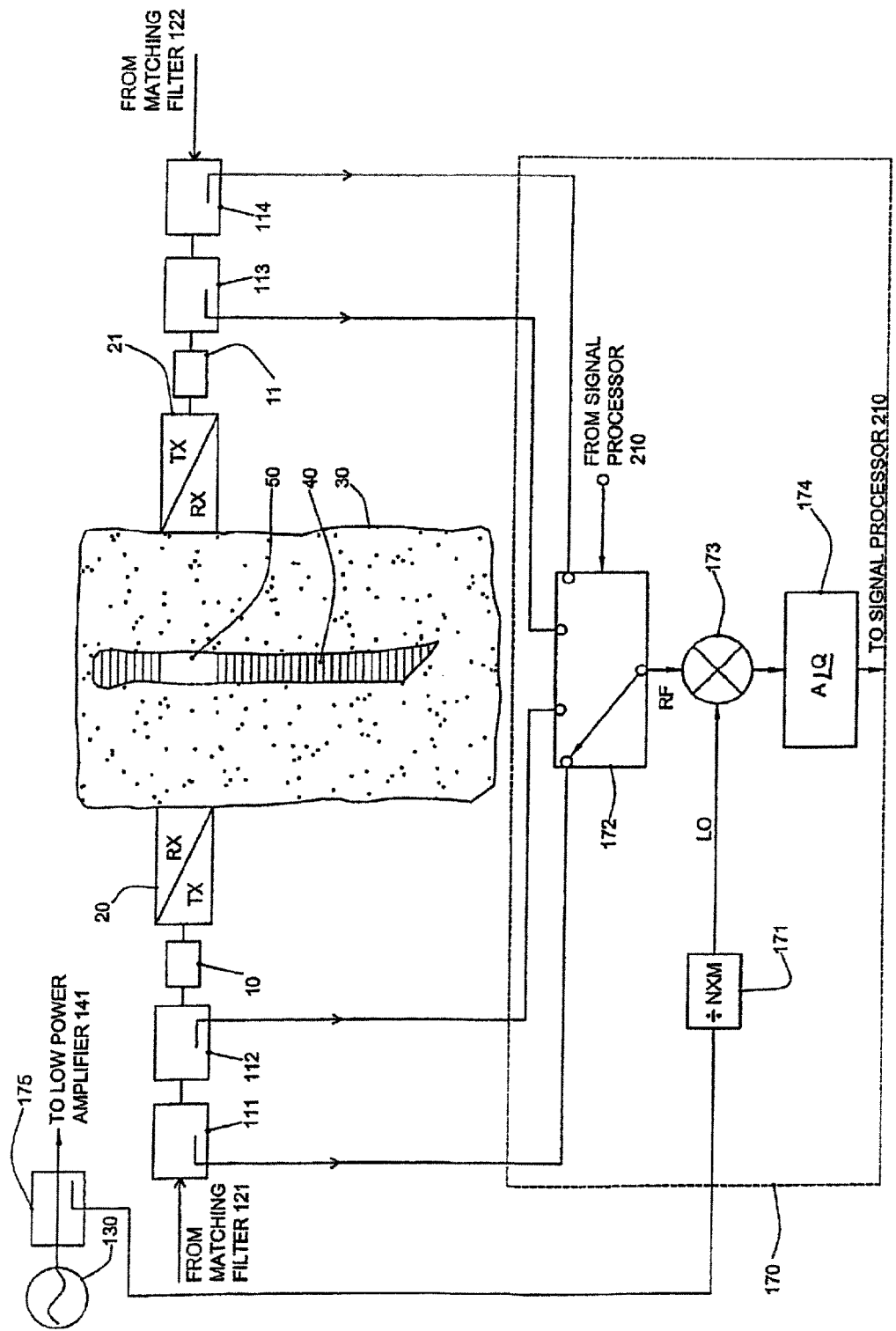
FIG. 5 schematically illustrates a detection scheme according to an embodiment of the present invention.

Details of a detection scheme that could be suitable for implementation in a portable hand-held instrument is given in FIG. 5. The detector 170 uses an electronically controlled single pole four throw switch (SP4T) 172, whose four inputs are taken from four directional couplers 111-114 and whose single output is fed into the first input port, the RF input, of an electronic signal mixer 173. The selection of the switch position of SP4T 172 is controlled by a control signal received from the signal processor 210. The second input to the electronic mixer 173, the local oscillator (LO) input, is derived from the input frequency source 130. The second signal path shown in FIG. 9 starts at the coupled port of forward power directional coupler 175, which is placed between the output of the frequency source 130 and the input to the first amplifier 141 (not shown here). The signal from the coupled port of 175 is fed into the input port of a frequency divider/multiplier device 171, where it is scaled in frequency. The output of the divider/multiplier device 171 is fed into the second port of the electronic mixer 173. The mixer 173 produces a signal at its output that is at a frequency which is the difference between the first input and the second input to 173. The output frequency, the intermediate frequency (IF), is then fed into the input of an amplitude/phase detector device 174, and the output from 174 is fed into the input of the signal processor 210. The description for all other components shown in FIG. 5 has already been given.

It should be noted here that the invention is not limited to using a reference signal in the second signal path that is derived from the input frequency source 130, and scaling of the reference signal may be carried out using other microwave devices and techniques known to a person skilled in the art. It should also be noted that the SP4T switch maybe replaced by two single-pole two-throw (SP2T) electronically controlled switches, or other similar devices known to a person skilled in the art. The input signal levels incident to the first and second inputs to the electronic mixer 172 may require conditioning, using either appropriate attenuator pads or amplifier blocks, in order to ensure that the first and second input signals to 172 are within the specified dynamic range of the selected electronic mixing device 172. It may also be necessary to place a filter between the output of the electronic mixer 173 and the input to the amplitude/phase detector 173. The filter would preferably take the form of a low pass filter, which would reject the sum of the two input frequencies (RF+LO) and allow the difference frequency (RF−LO) to pass through attenuated only by the insertion loss of the electronic mixer 173. The use of the detection scheme shown in FIG. 5 is not limited to the hand-held version of the instrument and maybe used in other system embodiments.

Figure 6:
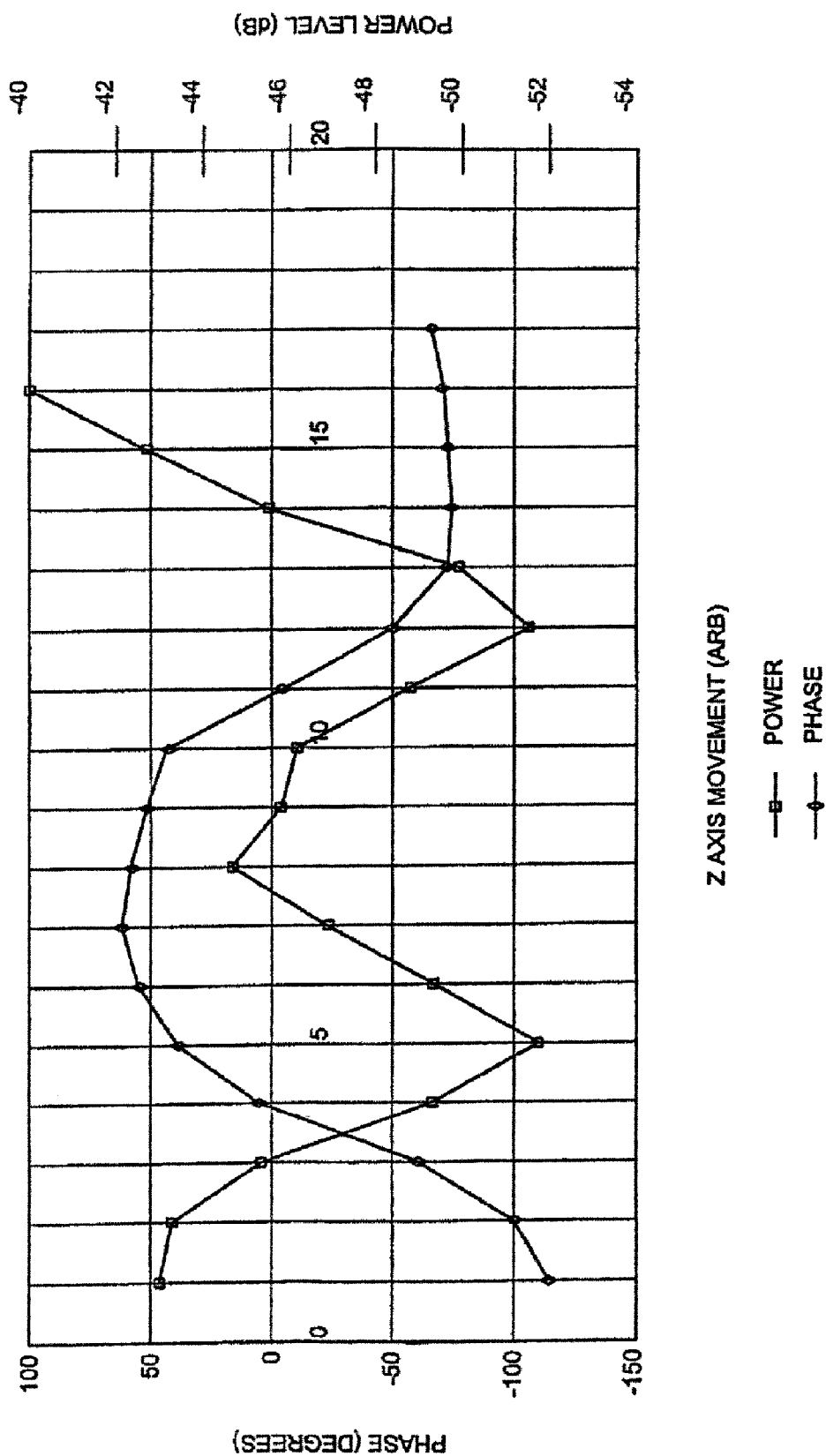
FIG. 6 shows an experimentally derived phase/magnitude response according an embodiment of the present invention.

In embodiments of the present invention the first and second antennas are mechanically arranged, for example by virtue of the frame or jig mentioned with reference to FIG. 1, such that they can be physically moved, either separately or together, with respect to the biological structure in which the implant is located whilst transmission between the two antennas is attempted. The phase and magnitude characteristics of the received signals vary as the position of the antennas relative to the implant varies. In particular, the phase and magnitude characteristics of the received signals vary relative to the location of the antennas with respect to the position of a locking pin hole in the implant. FIG. 6 illustrates the phase and magnitude response derived from an experimental arrangement according to the present invention in which a first antenna was moved relative to a locking nail, with a second antenna remaining stationary relative to the locking nail. As the two antennas became aligned over the centre of the locking nail a maximum phase shift occurs and this position corresponds to a peak in the magnitude response. Nulls also occur in the magnitude response.

A frequency source, or a plurality of the sources, that produces a low enough frequency to enable the signal to pass from a first antenna through one side of the biological tissue structure, the non-biological insert (through a channel or hole) and through the other side of the biological structure back into a second antenna, whilst ensuring that a high enough signal level (signal to noise ratio) is preserved at the detector to enable the signal to be differentiated from random, or non-deterministic, noise. It should be noted that the first or second antenna may not necessarily be located on the surface of the biological structure, but could be contained inside the structure via an insertion, or drill, hole; in this case the accumulated loss is reduced by virtue of the fact that the propagation distance is reduced, hence the signal-to-noise ratio will be greater.

For effective reflection measurements to be performed, it is ensured that the signal is able to reach the boundary between the biological structure (i.e. the bone) and discontinuity in the non-biological insert(s) (i.e. the edge of the locking hole of a metal insert), and then be reflected back to the first or second transmitting antenna and be of high enough signal level to enable the signal to be differentiated from random, or non-deterministic, noise. It should be noted that there may be asymmetry between the location of the insert and the biological structure, i.e. the insert may not be located at the centre of the biological structure.

This invention takes the above considerations into account by way of the fact that two solutions have been considered for the effective implementation of the final instrument; the specific solution chosen to implement the final instrument is dependant upon the end application(s) chosen. One solution makes use of a single frequency to measure both transmission and reflection characteristics and the other makes use of two frequencies, one to measure transmission and the other to measure reflection. The determining factors that must be established when deciding to use a single frequency, or a plurality of frequencies are based on the end application, i.e. drill hole diameter (or size of the discontinuity), location of insert in the biological system and the thickness of the tissue structure that constitutes the biological system. It should be noted that this invention is not limited to using two frequencies, but a plurality of frequencies may be used if or where appropriate. In this application we have limited the number of frequencies to two. It should be noted that this invention is not limited to using two antennas, a plurality of antennas could be used in applications where it may be required to quickly gather an array of information regarding the insert(s) located inside the biological system.

The microwave source(s) produce microwave energy at a frequency and power level that allow transmission of the energy through the biological system and any discontinuities in the non-biological insert, and in particular enable the microwaves to pass through the discontinuity, i.e. a through hole. In embodiments of the present invention the frequency may be in the range 1 GHz to 70 GHz, with a preferred frequency range being 1 GHz to 10 GHz. In laboratory experiments over the frequency range of 4 GHz to 7 GHz it was found that peak transmission of the microwave energy through tissue structures occurred at 5.05 GHz. At this frequency the power loss through tissue structures of varying thicknesses were as follows:

| Tissue Structure | Tissue Thickness (mm) | Power Loss (dB) |
| --- | --- | --- |
| Wrist | 21.2 | 31.78 |
| Lower Forearm | 32.3 | 47.70 |
| Mid-Forearm | 40.4 | 68.80 |
| Upper Forearm | 60.9 | 74.49 |
| Upper Arm (Biceps) | 100.0 | 84.32 |

If it is assumed that the incident power level is approximately 100 mW (20 dBm), which represents a safe continuous maximum power to avoid tissue damage from the microwaves themselves, then for the upper forearm the received power level will be approximately −55 dBm (20−75=−55), about 0.003 mW. Now, given that the theoretical limit placed on the signal that can be detected is around −144 dBm, which is governed by the thermal noise floor, with a good receiver it should be possible to resolve signals down to −100 dBm.

In embodiments of the present invention it is desired for the wavelength of the transmitted microwaves to be such that they propagate through the locking hole to be located in the implant. The diameter of the holes in femoral or tibial locking pins, for example, is typically in the range of 4-8 mm. The cylindrical holes will act as a cylindrical waveguide. The dominant mode of signal propagation through a cylindrical waveguide is known as the $TE_{11}$ mode, where the diameter of the waveguide required to enable signal propagation can be calculated as follows:

$$D = (2.4485\ C)/(\pi f_0 \sqrt{\mu_r \in_r})$$

Where:
C is the speed of light in a vacuum ($3 \times 10^8$ m/s)
$f_0$ is the frequency of operation (Hz)
$\mu_r$ is the relative permeability for a magnetic loading material (magnetic loading factor)
$\in_r$ is the relative permittivity for an electric loading material (dielectric loading factor)

The factor 2.4485 comes from the solution of the Bessel function for a cylindrical waveguide that supports the $TE_{11}$ mode of propagation and the calculation for the cut-off frequency for lowest insertion loss at the frequency of operation. For the experimental examples given above at a frequency of 5.05 GHz and assuming magnetic and dielectric loading factors of unity, i.e. propagation through free space, then the required waveguide diameter for signal propagation is 46.3 mm. This is much greater than the actual diameter of the locking holes in the locking nails, which are typically 4-8 mm in diameter. From the above equation the range of frequencies required to transmit through holes of this diameter is 29.2-58.5 GHz. However, at higher frequencies the loss through the tissue structures of the biological structure is much greater (as can be seen from Table 1 above, where at higher frequencies the penetration for a given power is reduced). Consequently higher incident power levels would be required at the higher frequencies. However, there is a practical power limit above which the incident microwave energy causes damage to the tissues of the biological structure.

To overcome this problem in preferred embodiments of the present invention the hole in the locking pin (or other implant) is filled with a solid or liquid dielectric loading element (shown in FIG. 7 as cross-hatching), which is preferably a biological (or biocompatible) substance. This has the effect of reducing the wavelength of the signal passing through the hole for any given frequency by a factor which is inversely proportional to the square root of product of the relative permittivity and the relative permeability ($\in_r$ and $\mu_r$ respectively) of the substance at the frequency of operation. In other words, the biocompatible substance has a dielectric loading factor $\in_r$ and or magnetic loading factor $\mu_r$ of greater than unity. Assuming that the hole diameter is 4 mm, this implies that the loading would need to be 133.98. This could be in the form of a dielectric material with a relative permittivity of 133.98, a magnetic material with a relative permeability of 133.98, or a combination of magnetic and dielectric materials where the product of the two permittivities is equal to 133.98. In preferred embodiments a biocompatible material, for example water or saline, is inserted inside the hole. It may be desirable to encapsulate the loading material inside a thin walled (or membrane) capsule made from a material that can be dissolved by the body, i.e. a capsule similar to that used to administer drags that are swallowed. The material used to load the hole may be solid or liquid so long as it is acceptable by the human or animal body.

In further embodiments it may be necessary to use a high microwave frequency for the signal to propagate through the pin hole (or other discontinuity). In this instance, it may be necessary for the amplifier(s) to be operated in a pulsed mode to enable higher peak powers to be used than those associated with normal continuous wave operation. In this mode of operation, a single pulse, or a train of low duty cycle pulses will be applied to the biological system to ensure that the average power level delivered into tissue is such that damage cannot occur to the biological structure. For example, a 10 W pulse of duration 1 ms with a total period of 100 ms (1% duty cycle) would produce an average power into tissue of 100 mW.

Figure 7:
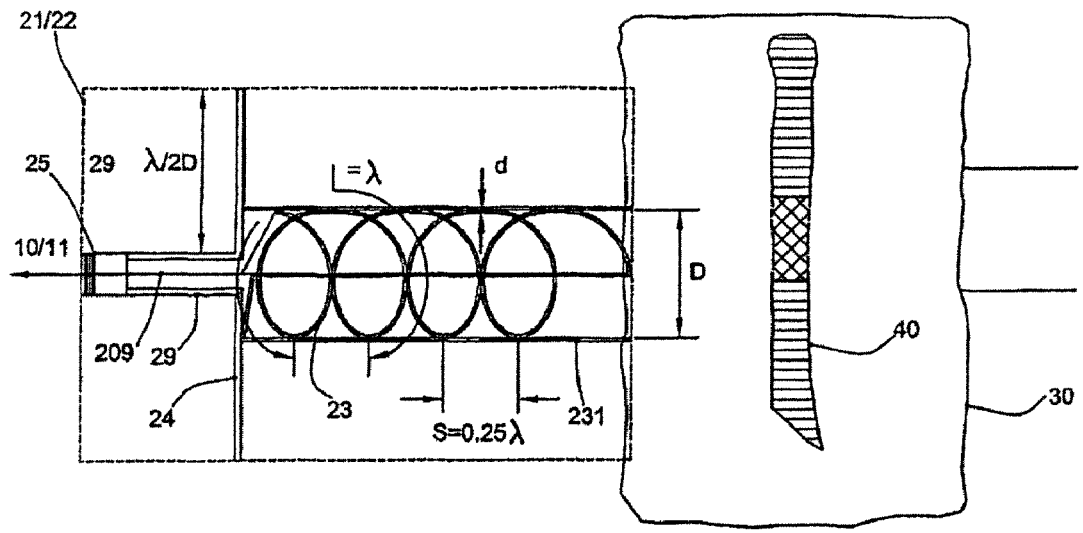
FIG. 7 shows a co-axially fed helical antenna.

A preferred antenna structure for use in embodiments of the present invention is a co-axially fed helical structure as shown in FIG. 7. A co-axial feed connector 25, which is preferably but exclusively an SMA type, is connected to the distal end of a flexible co-axial or waveguide cable assembly 10,11, whose proximal end is connected to the other associated electronic instrumentation, which has already been described in detail. The helical construction consists of a circular plate 24, connected to an outer conductor of a co-axial feed 29. The circular plate acts as a return for a circularly would helix 23 and is known as a reflector. The preferred diameter of the plate 24 is given by the wavelength of the frequency of operation divided by twice the outside diameter of the helix 23 ($\lambda/2D$). The inner conductor of the co-axial feed 209 is connected to a start of the helical winding 23 and the end (finish) of the helical winding 23 is returned through the centre of the winding, which is electrically connected to the circular plate 24. The preferred length of the helical winding 23 is six times the wavelength of operation ($6\lambda$), and the spacing between adjacent turns (S) is determined by $0.25\lambda$. The preferred diameter (D) of the windings is given by $D=\sqrt{((2S/\lambda)+1)}$ and the pitch of the windings is between 12° and 15°, which is determined by S. The length (L) of each turn is between $0.75\lambda$ and $1.4\lambda$, with the preferred length being $1\lambda$. The helical winding 23 is placed inside a non-metallic tube 231 to enable the winding to maintain its form. It is preferred that the end of the tube 231 is sealed to prevent fluid (or other substances) from getting inside the tube and affecting the performance of the overall antenna structure. The distal end of tube 231 may be placed in contact with the biological structure 30. The material used for the tube should exhibit low loss (low tan $\delta$) at the frequency of operation. It is theoretically possible to use the helical antenna construction to achieve a beam-width of as low as 22° and a power gain referenced to an isotropic radiator of up to 19 dBi. A material with a low conductor loss should be used for winding the helix. Preferred materials are silver wire, copper wire and silver plated wire. The structure shown in FIG. 7 may be kept rigid by using silver plated stainless steel wire, where the plating thickness is at least three skin depths deep at the frequency of operation.

Figure 8:
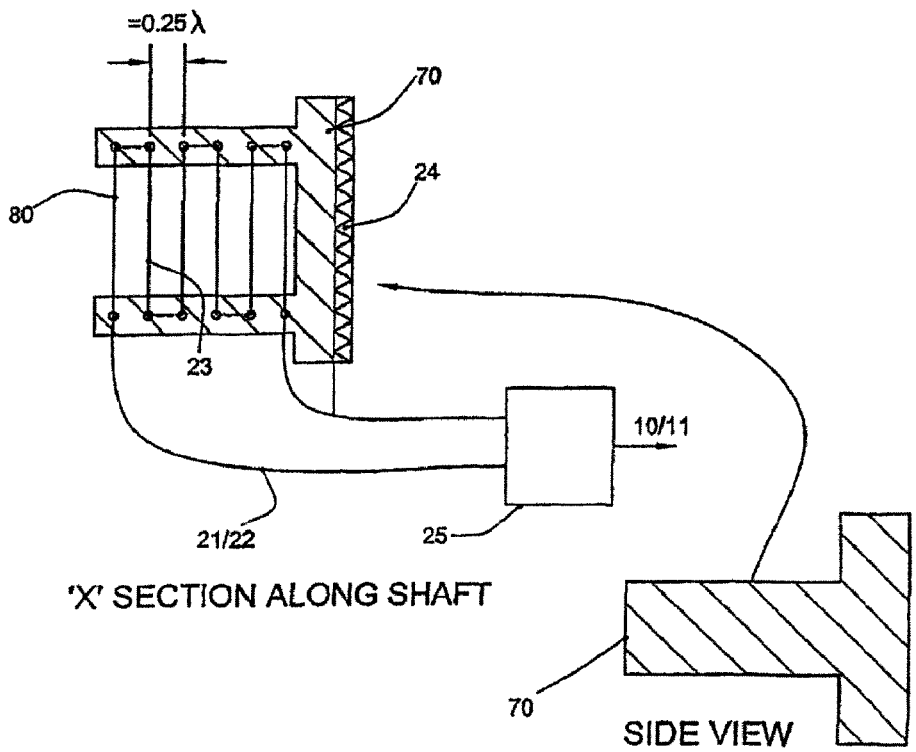
FIG. 8 shows the helical antenna of FIG. 7 wound inside the walls of the guide tube.

FIG. 8 shows the helical antenna construction 23 of FIG. 7 fitted inside a guide tube 70 to form an integral part of the tube. In this aspect of the invention the helical winding is contained inside the walls of the tube 70, where the design parameters associated with the helical antenna construction, as detailed in the description given for FIG. 7, have been taken into account. In this arrangement it is not practical for one end of the winding to be returned through the centre of the helix, therefore the two ends (the start and the finish) of the windings protrude through the wall of the guide tube 70. The return plate (reflector) 24 is attached to the proximal end of the guide tube 70 and may take the form of a metallic coating or a separate metal disk. The plate 24 will contain a hole whose diameter is the same as that of the guide tube 70 to enable assess into the tube to enable, for example, a drill bit or another measurement probe to be inserted for the purpose of gaining access to the biological structure 30 or object (insert) 40. First end of helical winding 23 is attached to plate 24, which is also attached to outer conductor of co-axial feed 29. Second end of helical winding 23 is attached to inner conductor of co-axial feed 209 and both conductors 29, 209 are connected to co-axial feed connector 25. In this arrangement the finish of the helical antenna winding 23, located at the distal end, is returned either along the outer wall of the guide tube 70 where a sleeve (not shown) is inserted over the outside wall of the guide tube, or alternatively, the wire is contained inside the wall of the guide tube via a channel cut in the wall near to the outer surface of tube 70.

Figure 9:
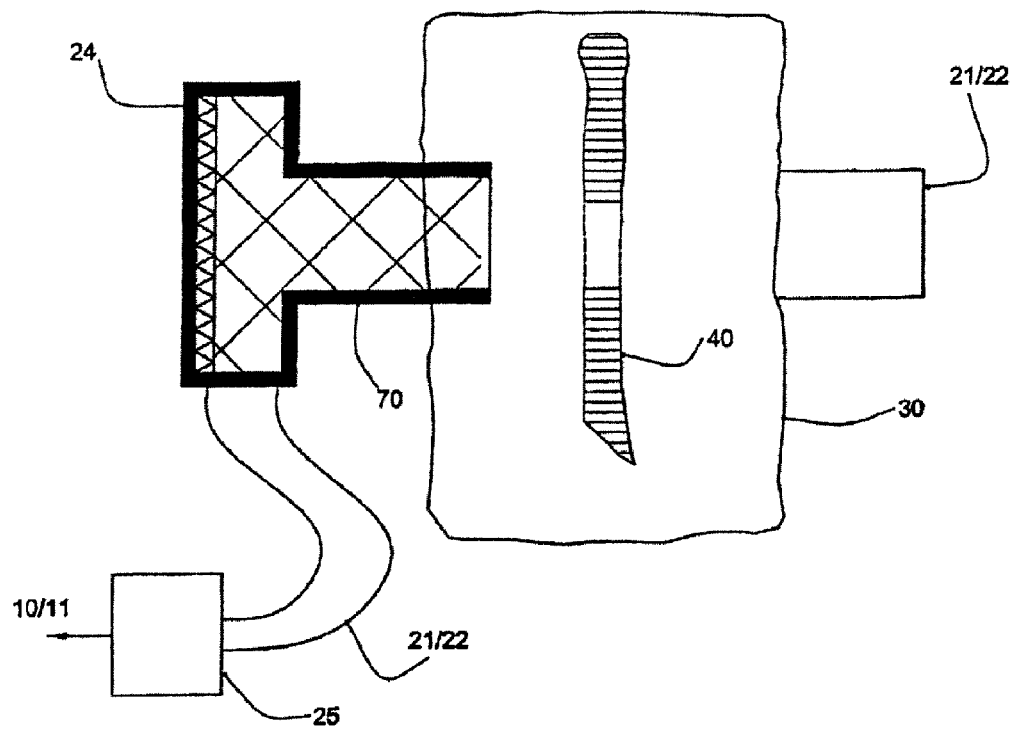
FIG. 9 shows the helical antenna wound inside the guide tube and inserted inside the biological system in close proximity to the non-biological object.
Figure 10:
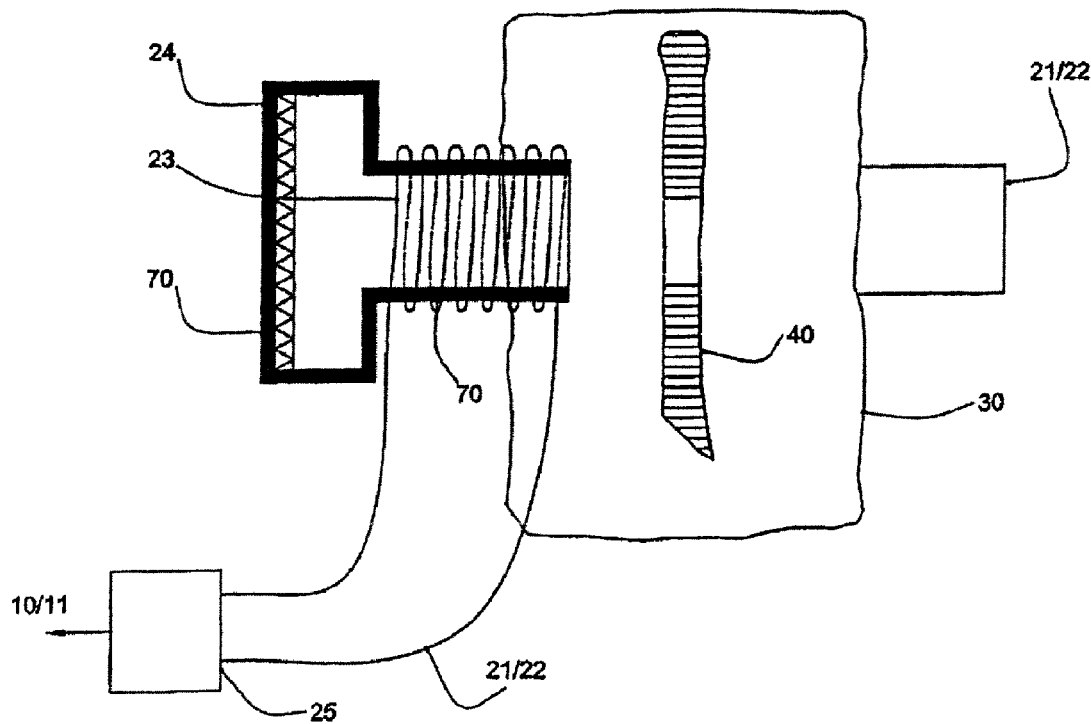
FIG. 10 shows the helical antenna wound on the outside of the guide tube and inserted inside the biological system in close proximity to the non-biological object.

FIG. 9 shows the same structure as described with reference to FIG. 8 with the exception that the integrated antenna and guide tube are located inside the biological structure 30. The structure is sealed to ensure that fluid ingress (or other) cannot reach the helical antenna winding 23 and cause interference with the operation of the antenna structure 20,21. It is preferred that the material used for constructing the guide tube is non conductive and is low loss to microwave energy at the frequency of operation. The material should also be biocompatible to allow for insertion inside the human body. FIG. 10 shows an arrangement where the helical antenna winding 23 is would on the outside of the guide tube 70. In this arrangement it may be preferable to fit a non-conducting sleeve, such as a heat shrink sleeve, over the outside of the helical winding 23. The sleeve is preferably made from a material, which is biocompatible. The advantage of the arrangement shown in FIG. 10 is that it is easier to manufacture the antenna 20,21 due to the winding not being embedded inside the guide tube 70. All other aspects of the design shown in FIG. 10 have been addressed in the descriptions associated with FIGS. 7 to 9 above. Other forms of antenna known to the person skilled in the art may be used in embodiments of the present invention, for example isotropic radiators or horn antennas. A loaded inverse horn antenna may preferably be used in some embodiments.

According to a further alternative embodiment of the present invention the microwave transmitter and receiver is of the 'Impulse' type. Impulse systems are also known as 'Ultra wideband', 'Carrier-free' and 'Baseband' systems. An Impulse system generates a burst of microwave energy of extremely short duration. This microwave energy is of a broad spectrum and is likely to extend across all or part of the range from 3.1 GHz to 10.6 GHz. The burst of microwave radiation is repeated at intervals at a high pulse repetition frequency and is transmitted through the biological material. By employing very short pulses the position of the non-biological material can be determined with high resolution and accuracy. This may be achieved by, for example, time gating.

Figure 11:
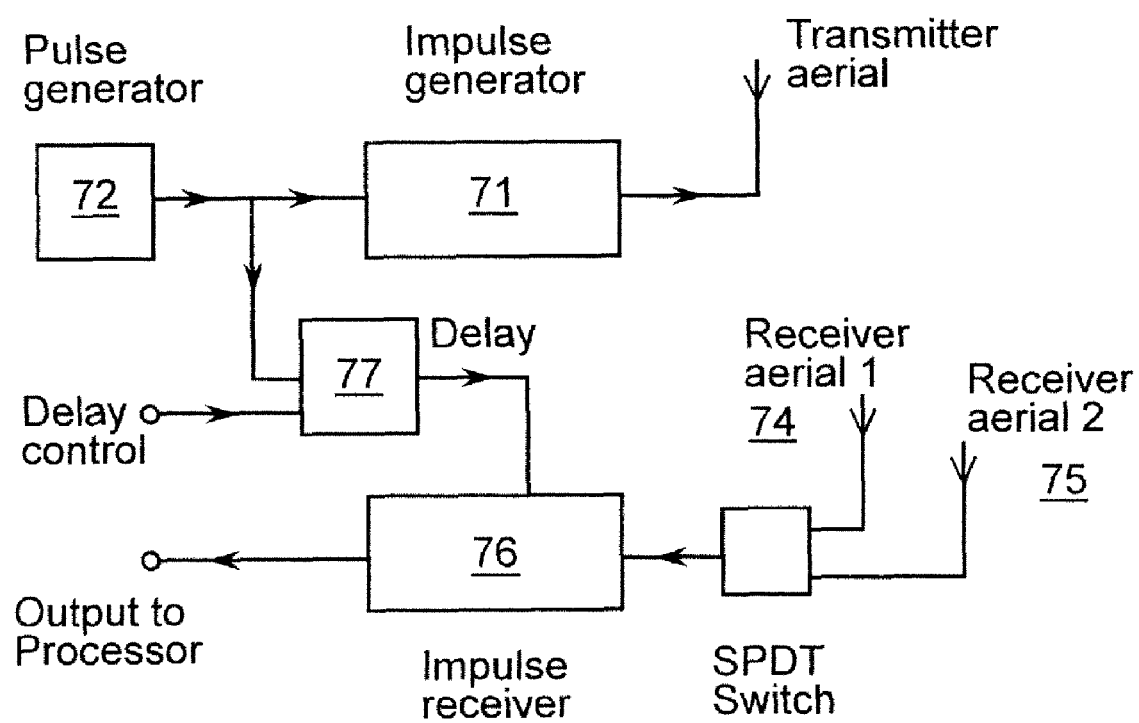
FIG. 11 schematically illustrates an impulse generation system for use with embodiments of the present invention.

A simplified block diagram of an Impulse system is illustrated in FIG. 11. The short bursts of wideband microwave radiation are produced by circuitry referred to as an impulse generator 71, the design of which will be known to a skilled person. The impulse generator is in turn triggered from a pulse generator 72 such that a rapid succession of impulses is created. The pulsed microwave radiation is then transmitted from a suitable aerial 73 connected to the output of the impulse generator. The received radiation is received by a similar aerial 74/75 that is connected to the input of an impulse receiver circuit 76, which detects the received pulses at a set time after the impulse generator 71 was triggered. A time delay circuit 77 is used for this purpose such that this delay can be varied and is controlled via an input signal derived from the system. The time delay between the transmitted pulse and the received pulse is directly proportional to the distance to the non-biological material that produced the reflection. In this way a time gating technique provides a precision distance measurement. FIG. 7 shows two receiver aerials. This is to accommodate both reflection and transmission measurements. The outputs from the two aerials would be separately directed to the Impulse receiver using a single pole double throw switch as shown.

The type of antennae suitable for use in this embodiment of the present invention is a wideband antenna that will be selected for their suitability to transmit and receive fast pulses of microwave radiation. The antennae have the property of being able to radiate short pulses of microwave radiation while having low "ringing" characteristic and also have the property of having a very low variation in time delay across the microwave frequency band. This latter property is to prevent spreading the pulse out in time which would degrade the measurement precision.

The invention claimed is:

1. Apparatus for detecting a discontinuity within a non-biological element located within a biological structure, the apparatus comprising:
   a microwave energy source;
   a first antenna coupled to the microwave energy source and arranged to transmit the microwave energy into the biological structure;
   a second antenna arranged to receive at least a portion of the transmitted microwave energy;
   an antenna carrier arranged to have the first and second antenna affixed thereon and including means for moving the first and second antenna with respect to the biological structure; and
   a signal processing unit coupled to the second antenna and arranged to determine the phase and/or magnitude response of the received microwave energy as a function of the position of the antennas with respect to the biological structure and provide an indication of the location of the discontinuity within the non-biological element located within the biological tissue according to the phase and/or magnitude response.

2. Apparatus according to claim 1, wherein the signal processing unit is arranged to determine the phase and/or magnitude response of the received microwave energy corresponding to a plurality of positions of the antenna relative to the biological structure and to process the determined phase and/or magnitude responses to generate image data of the discontinuity.

3. Apparatus according to claim 2, wherein the signal processing un arranged to apply scanning radar techniques to generate the image data.

4. Apparatus according to claim 1, wherein the first antenna is also arranged to receive at least a portion of the transmitted microwave energy and the second antenna is also coupled to the microwave energy source and arranged to transmit the microwave energy into the biological structure.

5. Apparatus according to claim 1, wherein the signal processing unit is arranged to determine the phase and/or magnitude response of the microwave energy transmitted from one antenna to the other and the phase and/or magnitude response of the microwave energy reflected back to the same antenna it was transmitted from.

6. Apparatus according to claim 1, wherein the location of the discontinuity is given by the relative position of the antennas and the biological structure where a peak or null in the magnitude response of the received microwave energy is detected.

7. Apparatus according to claim 1 further comprising a plurality of microwave energy sources and switching means for selecting one or more of the plurality of microwave energy sources.

8. Apparatus according to claim 7, wherein the plurality of microwave energy sources are arranged to generate microwave energy at different frequencies.

9. Apparatus according to claim 1, wherein the microwave energy source is arranged to generate microwave energy across a plurality of frequencies.

10. Apparatus according to claim 9, wherein the microwave energy source comprises an impulse system.

11. Apparatus according to claim 1, wherein the signal processor is arranged to perform two port transmission and reflection measurements of the microwave energy.

12. Apparatus according to claim 1, wherein the discontinuity comprises a cylindrical hole and the microwave energy source is arranged to generate the microwave energy at a frequency or range of frequencies at which the wavelength of the microwave energy propagated through biological structure and discontinuity is such that the cylindrical hole functions as a cylindrical waveguide.

13. Apparatus according to claim 12, wherein the apparatus further comprises a dielectric loading element arranged to be inserted within the discontinuity.

14. Apparatus according to claim 13, wherein the dielectric loading element has a relative permittivity substantially equal to or greater than the surrounding biological structure.

15. Apparatus according to claim 1, wherein the microwave energy source is arranged to generate the microwave energy in a pulsed mode.

16. Apparatus according to claim 1, wherein at least one of the first and second antennas comprises a helical antenna arranged to be inserted within the biological structure.

17. Apparatus according to claim 16, wherein at least a portion of the helical antenna is mounted within a guide tube, the guide tube being made from a biocompatible material.

18. Apparatus according to claim 17, wherein the helical antenna comprises a helical winding, the winding being located within the guide tube.

19. A method of detecting a discontinuity within a non-biological element located within a biological structure, the method comprising:
   transmitting microwave energy into the biological structure from a first antenna;
   receiving at least a portion of the transmitted microwave energy at a second antenna;
   moving the first and second antenna with respect to the biological structure; and
   measuring the received microwave energy and determining the phase and/or magnitude response of the received microwave energy as a function of the position of the antennas with respect to the biological structure and providing an indication of the location of the discontinuity within the non-biological element located within the biological tissue according to the phase and/or magnitude response.

20. The method of claim 19, wherein the phase and/or magnitude response of the received microwave energy is determined at a plurality of positions of the antenna relative to the biological structure and are processed to generate image data of the discontinuity.

21. The method of claim 20, wherein the image data is generated by apply scanning radar techniques.

22. The method of claim 19, wherein at least a portion of the transmitted microwave energy is also received at the first antenna and at least a portion of the transmitted microwave energy is also transmitted from the second antenna.

23. The method of claim 19, wherein the determined phase and/or magnitude response includes the phase and/or magnitude response of the microwave energy transmitted from one antenna to the other and the phase and/or magnitude response of the microwave energy reflected back to the same antenna it was transmitted from.

24. The method of claim 19, wherein the location of the discontinuity is given by the relative position of the antennas and the biological structure where a peak or null in the magnitude response of the received microwave energy is detected.

25. The method of claim 19 further comprising selecting one or more of a plurality of microwave energy sources for transmission into the biological structure.

26. The method of claim 25, wherein the plurality of microwave energy sources generate microwave energy at different frequencies.

27. The method of claim 19, wherein the microwave energy is generated across a plurality of frequencies.

28. The method of claim 27, wherein the microwave energy is generated by an impulse system.

29. The method of claim 19 further comprising performing two port transmission and reflection measurements of the microwave energy.

30. The method of claim 19, wherein the discontinuity comprises a cylindrical hole and the method further comprises loading the hole with a dielectric loading element.

31. The method of claim 30, wherein the dielectric loading element has a relative permittivity substantially equal to or greater than the surrounding biological structure.

32. The method of claim 19, wherein the microwave energy is generated in a pulsed mode.

33. The method of claim 19, wherein at least one of the first and second antennas comprises a helical antenna inserted within the biological structure.

34. The method of claim 33, wherein at least a portion of the helical antenna is mounted within a guide tube, the guide tube being made from a biocompatible material.

35. The method of claim 19, wherein the non-biological element comprises an intramedullary nail and the discontinuity comprises a locking hole within the nail.

* * * * *

UNITED STATES PATENT AND TRADEMARK OFFICE
CERTIFICATE OF CORRECTION

PATENT NO.        : 8,049,516 B2                                  Page 1 of 1
APPLICATION NO.   : 12/278112
DATED             : November 1, 2011
INVENTOR(S)       : Christopher P. Hancock et al.

It is certified that error appears in the above-identified patent and that said Letters Patent is hereby corrected as shown below:

On the Cover Page:

At field (73), "Creo Medical Llimited" should be -- Creo Medical Limited --

Signed and Sealed this
Sixth Day of March, 2012

David J. Kappos
*Director of the United States Patent and Trademark Office*

UNITED STATES PATENT AND TRADEMARK OFFICE
CERTIFICATE OF CORRECTION

PATENT NO. : 8,049,516 B2
APPLICATION NO. : 12/278112
DATED : November 1, 2011
INVENTOR(S) : Christopher P. Hancock et al.

It is certified that error appears in the above-identified patent and that said Letters Patent is hereby corrected as shown below:

On the Cover Page, Item (73) Assignee:

"Microoncology Limited" should be deleted.

Signed and Sealed this
Thirty-first Day of July, 2012

David J. Kappos
*Director of the United States Patent and Trademark Office*

UNITED STATES PATENT AND TRADEMARK OFFICE
CERTIFICATE OF CORRECTION

PATENT NO. : 8,049,516 B2
APPLICATION NO. : 12/278112
DATED : November 1, 2011
INVENTOR(S) : Christopher P. Hancock et al.

Page 1 of 1

It is certified that error appears in the above-identified patent and that said Letters Patent is hereby corrected as shown below:

In the Claims:

At Column 15, line 50, "un" should be -- units is --.

Signed and Sealed this
Twenty-sixth Day of March, 2013

Teresa Stanek Rea
*Acting Director of the United States Patent and Trademark Office*